(12) United States Patent
Case (10) Patent No.: US 8,292,938 B2
(45) Date of Patent: Oct. 23, 2012

(54) PLACEMENT OF MULTIPLE INTRALUMINAL MEDICAL DEVICES WITHIN A BODY VESSEL

(75) Inventor: Brian C. Case, Bloomington, IN (US)

(73) Assignee: Cook Medical Technologies LLC, Bloomington, CO (US)

( * ) Notice: Subject to any disclaimer, the term of this patent is extended or adjusted under 35 U.S.C. 154(b) by 2115 days.

(21) Appl. No.: 11/210,999

(22) Filed: Aug. 24, 2005

(65) Prior Publication Data

US 2006/0047297 A1   Mar. 2, 2006

Related U.S. Application Data

(60) Provisional application No. 60/605,313, filed on Aug. 27, 2004.

(51) Int. Cl.
  *A61M 29/00* (2006.01)
(52) U.S. Cl. ......... 623/1.11; 623/1.1; 623/2.1; 623/2.11
(58) Field of Classification Search ................ 623/1.1, 623/1.11, 1.12, 1.22, 1.23, 2.1, 2.11, 2.17, 623/2.18
See application file for complete search history.

(56) References Cited

U.S. PATENT DOCUMENTS

| | | | |
|---|---|---|---|
| 4,564,014 A | 1/1986 | Fogarty | |
| 4,580,568 A | 4/1986 | Gianturco | |
| 5,133,725 A * | 7/1992 | Quadri | 606/159 |
| 5,607,465 A | 3/1997 | Camilli | |
| 5,609,598 A | 3/1997 | Laufer et al. | |
| 5,662,675 A | 9/1997 | Polansky, Jr. et al. | |
| 5,810,847 A | 9/1998 | Laufer et al. | |
| 5,824,041 A | 10/1998 | Lenker et al. | |
| 5,833,694 A | 11/1998 | Poncet | |
| 6,022,359 A | 2/2000 | Frantzen et al. | |
| 6,077,295 A * | 6/2000 | Limon et al. | 623/1.11 |
| 6,110,191 A | 8/2000 | Dehdashtian | |
| 6,126,685 A * | 10/2000 | Lenker et al. | 623/1.11 |
| 6,143,016 A * | 11/2000 | Bleam et al. | 606/198 |
| 6,200,336 B1 * | 3/2001 | Pavcnik et al. | 623/1.15 |
| 6,231,598 B1 | 5/2001 | Berry et al. | |
| 6,287,334 B1 * | 9/2001 | Moll et al. | 623/1.24 |
| 6,299,635 B1 | 10/2001 | Frantzen | |
| 6,299,637 B1 | 10/2001 | Shaolian | |
| 6,464,720 B2 | 10/2002 | Boatman et al. | |
| 6,508,833 B2 | 1/2003 | Pavcnik et al. | |
| 2001/0039450 A1 | 11/2001 | Pavcnik et al. | |
| 2002/0029994 A1 | 3/2002 | Schon | |
| 2002/0123786 A1 | 9/2002 | Gittings | |
| 2002/0179098 A1 * | 12/2002 | Makower et al. | 128/898 |
| 2003/0014104 A1 | 1/2003 | Cribier | |
| 2003/0055492 A1 * | 3/2003 | Shaolian et al. | 623/1.24 |
| 2003/0135266 A1 * | 7/2003 | Chew et al. | 623/1.16 |
| 2004/0015230 A1 * | 1/2004 | Moll et al. | 623/1.24 |
| 2004/0093061 A1 * | 5/2004 | Acosta et al. | 623/1.11 |

FOREIGN PATENT DOCUMENTS

| | | |
|---|---|---|
| WO | WO 96/37167 A | 11/1996 |
| WO | WO 98/22045 A | 5/1998 |
| WO | WO/03/101346 | 12/2003 |

* cited by examiner

*Primary Examiner* — Corrine M McDermott
*Assistant Examiner* — Mark Mashack
(74) *Attorney, Agent, or Firm* — Buchanan Nipper (57) ABSTRACT

Medical device delivery systems and related kits and methods for placing multiple expandable medical devices within a body vessel are provided. A delivery system includes first and second expandable medical devices having the same or different dimensions. Placement of the first and second expandable medical devices in a body vessel can be achieved without requiring withdrawal of one or more components of the delivery system and insertion of secondary components.

15 Claims, 7 Drawing Sheets

PLACEMENT OF MULTIPLE INTRALUMINAL MEDICAL DEVICES WITHIN A BODY VESSEL

CROSS REFERENCE TO RELATED APPLICATION

This application claims priority to U.S. Provisional Application Ser. No. 60/605,313 filed on Aug. 27, 2004, the disclosure of which is hereby incorporated into this disclosure in its entirety.

FIELD OF THE INVENTION

The invention relates to intraluminal medical devices, generally, and their placement within body vessels.

BACKGROUND OF THE INVENTION

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990's. Coronary and peripheral stents have been proven to provide a superior means of maintaining vessel patency, and have become widely accepted in the medical community. Furthermore, the use of stents has been extended to treat aneurysms and to provide occlusion devices, among other uses.

Typically, intraluminal medical devices, such as stents, are deployed at a point of treatment in a body vessel by a delivery device that has been directed through the body vessel. Once the intraluminal device has been deployed at the point of treatment, the delivery device is withdrawn from the vessel. Using prior art devices and methods, it is necessary to insert a second delivery device following removal of the first if deployment of an additional intraluminal device is desired. Each additional intraluminal medical device for deployment in the vessel necessitates an additional delivery device. Each additional delivery device, like the first, must be directed through the body vessel to a point of treatment, which increases the length and complexity of the procedure.

Recently, prosthetic valves that can be placed in a body vessel using minimally invasive techniques have developed in the art. These valves are designed to replace or supplement the function of incompetent natural valves. Considering the presence of multiple natural valves along the length of some body vessels, it may be necessary in some treatments to deliver multiple prosthetic valves into a single vessel. For example, some veins include multiple natural venous valves along some portions of their length. In treatments for replacing or supplementing the function of natural venous valves, such as a treatment for venous insufficiency, it may be desirable to place multiple prosthetic valves along a portion of a vein. Unfortunately, the prior art does not teach any suitable devices or methods for the delivery of multiple intraluminal medical devices without necessitating withdrawal of a first delivery device from the vessel and insertion of a second delivery device into the vessel for each additional intraluminal device being delivered.

Therefore, there is a need for medical devices and methods that allow for the deployment of multiple intraluminal medical devices in a body vessel without the need for retracting a delivery device from the vessel and inserting a second delivery device into the vessel between deployments.

SUMMARY OF EXEMPLARY EMBODIMENTS OF THE INVENTION

The invention provides delivery systems for placing multiple medical devices within a body vessel. In one exemplary embodiment, a delivery system according to the invention comprises an elongate member with proximal and distal ends and first and second mounting regions. A first expandable medical device is disposed on the first mounting region and a second expandable medical device is disposed on the second mounting region. A sheath is disposed over at least a portion of the elongate member and the first and second expandable medical devices. The first expandable medical device has a first dimension that is suitable for a first point of treatment within the body vessel and the second expandable medical device has a second dimension that is suitable for a second point of treatment within the body vessel. The first and second dimensions can be the same.

In another exemplary embodiment, a delivery system according to the invention comprises an elongate member with a proximal end, a distal end, a proximal mounting region, and a distal mounting region. A first prosthetic valve is disposed on the proximal mounting region and a second prosthetic valve is disposed on the distal mounting region. The first prosthetic valve has a first dimension that is suitable for a first point of treatment in the body vessel and the second prosthetic valve has a second, different dimension that is suitable for a second point of treatment in the body vessel. A sheath is disposed over at least a portion of the elongate member and the first and second prosthetic valves.

The invention also provides kits. In one exemplary embodiment, a kit according to the invention comprises an elongate member with proximal and distal ends and having first and second mounting regions. The kit also includes first and second expandable medical devices, and a means for compressing the first and second expandable medical devices onto the first and second mounting regions. The first and second expandable medical devices can have the same or different dimensions.

The invention also provides methods of supplying medical devices for implantation within a body vessel. One exemplary method according to the invention comprises the steps of accepting a request from a user for medical devices, collecting data relating to first and second points of treatment within a body vessel, selecting a first medical device based on the data relating to the first point of treatment, and selecting a second medical device based on the data relating to the second point of treatment. Another step of the method comprises assembling a delivery system that comprises the first and second medical devices. Another step of the method comprises providing the delivery system to the user.

The invention also provides methods of supplying prosthetic valves for implantation in a body vessel. One exemplary method according to the invention comprises the steps of accepting a request for prosthetic valves from a user and collecting data relating to first and second points of treatment within a body vessel. The method also includes the steps of selecting a first prosthetic valve having a first dimension suitable for the first point of treatment and selecting a second prosthetic valve having a second dimension suitable for the second point of treatment. The method also includes the steps of placing the first and second prosthetic valves in a delivery system in a predetermined order and providing the delivery system to the user.

Additional understanding of the invention can be obtained with review of the description of exemplary embodiments appearing below and reference to the appended drawings.

DETAILED DESCRIPTION OF EXEMPLARY EMBODIMENTS OF THE INVENTION

The following provides a detailed description of various exemplary embodiments of the invention. The embodiments described and illustrated herein are exemplary in nature, and serve simply as examples to aid in enabling one of ordinary skill in the art to make and use the invention. The description and illustration of exemplary embodiments are not intended to limit the invention, or its protection, in any manner.

Figure 1:
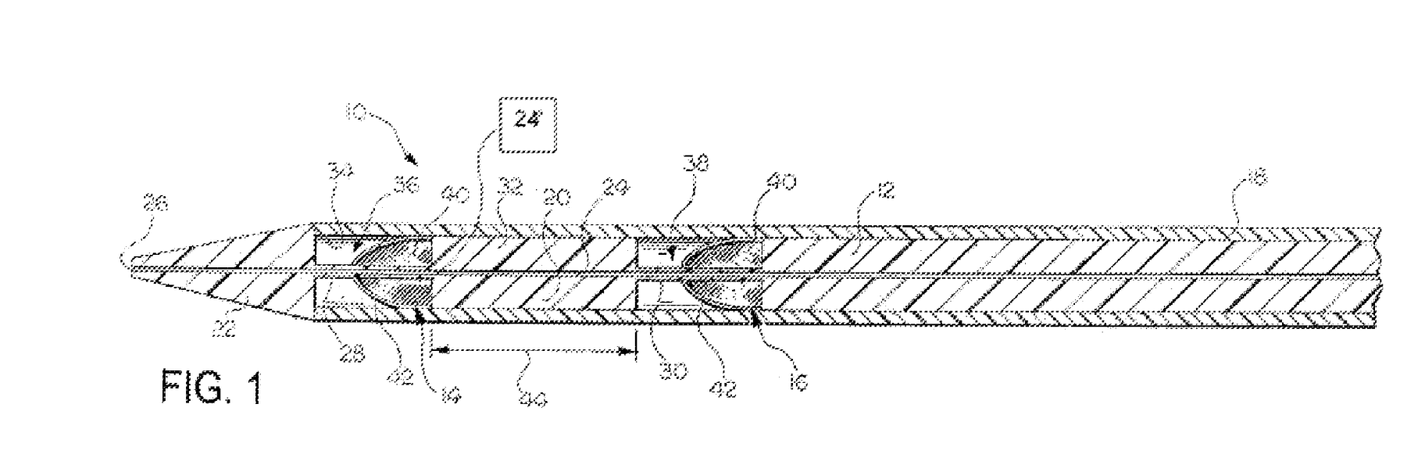
FIG. 1 is a sectional view of a delivery system according to a first exemplary embodiment of the invention.

The invention provides delivery systems for placing medical devices within a body vessel. FIG. 1 illustrates a delivery system 10 according to a first exemplary embodiment of the invention. The delivery system 10 includes an elongate member 12, a first expandable medical device 14, a second expandable medical device 16, and a sheath 18 disposed over the elongate member 12 and the expandable medical devices 14, 16.

The elongate member 12 can be any elongate member suitable for use with expandable medical devices, such as a dilator or catheter. In the illustrated embodiment, the elongate member 12 includes a main body 20 and a tapered distal end 22. The tapered distal end 22 facilitates the introduction of the elongate member 12 and the delivery system 10 into a body vessel, and their navigation through the body vessel to one or more points of treatment. The proximal end (not illustrated in FIG. 1) typically remains outside of the body vessel during use, and can include any suitable handle, connector, or other desirable structure.

A passageway 24 extends from the distal end 22 to the proximal end, and can receive a wireguide (not illustrated in FIG. 1). As used herein, the term "wireguide" refers to elongate members used in minimally invasive procedures to define a path along which other devices can be advanced. The term is considered equivalent in meaning to the term "guidewire" as used in the art. An opening 26 in the distal end 22 provides communication between the passageway 24 and the environment external to the elongate member 12. The opening 26 can be used for insertion of a wireguide into the passageway 24. In this configuration, the elongate member 12 can be navigated over a previously placed guidewire to achieve placement of the expandable medical devices 14, 16 at desired points of treatment within a body vessel. It is noted that while the passageway 24 extends along the entire length of the elongate member 12 in FIG. 1, an alternative passageway 24', such as one that extends along only a portion of the length of the elongate member 12, can be used. Accordingly, it is noted that the invention can be applied to both over-the-wire and rapid exchange type delivery systems and components.

The elongate member 12 defines mounting regions 28, 30 that can receive the expandable medical devices 14, 16. In this embodiment, the mounting regions 28, 30 are portions of the elongate member 12 main body 20 that have a reduced diameter as compared to other portions of the main body 20, such as intermediate portion 32. The expandable medical devices 14, 16 can be associated with the mounting regions 24, 26 in any suitable manner, including being disposed on, over and around the mounting regions 24, 26. The specific nature of the spatial relationship between the expandable medical devices 14, 16 and the mounting regions 24, 26 will depend on the type of expandable medical device used with each region 24, 26. In the embodiment illustrated in FIG. 1, the mounting regions 28, 30 of the elongate member 12 individually cooperate with an inner surface 34 of the sheath 18 to define chambers 36, 38. The expandable medical devices 14, 16 are disposed on the chambers 36, 38 in the assembled delivery system 10.

The elongate member 12 can be formed of any suitable material or materials, including biocompatible plastics. As illustrated in FIG. 1, the elongate member 12 can comprise an integral member formed or altered in a manner that provides the desired structural features, including the mounting regions 28, 30 and intermediate portion 32. Alternatively, the elongate member 12 can be formed of several components. In one exemplary embodiment, a series of components, such as a tip member, one or more optional chamber members, and one or more intermediate members are placed in sequence on a tubular member to form the elongate member. The placement of the components on the tubular member can be a coaxial placement. The individual components can be secured to the tubular member if desired.

The expandable medical devices 14, 16 can be any suitable type of expandable medical device, including stents, filters, distal protection devices, occluders, prosthetic valves, and other expandable medical devices that can be delivered to a point of treatment within a body vessel. The expandable medical devices 14, 16 can be self-expandable or can require application of an outwardly directed force to effect expansion, such as balloon-expandable devices. Also, in any given delivery system according to the invention, the expandable medical devices 14, 16 can be the same type of device, or different types can be used. For example, both devices can be prosthetic valves, or a single prosthetic valve can be used with a stent or other desirable type of device. The types of devices chosen will depend on several factors, including the nature of the treatment in which the devices 14, 16 and the delivery system 10 are being used.

Delivery systems according to the invention are particularly well suited for use in deployment of self-expandable medical devices. Accordingly, a self-expandable medical device can be disposed on one or both of the mounting regions 24, 26 of the elongate member 12. Any suitable type of self-expandable medical device can be used with the delivery systems according to the invention, including self-expandable stents, prosthetic valves that include a self-expandable support frame, such as prosthetic valves for implantation in a vein (prosthetic venous valves), self-expandable filters, self-expandable distal protection devices, self-expandable vessel occluders, and other self-expandable devices. Suitable self-expandable medical devices for use with delivery systems according to the invention include those described in U.S. Pat. No. 6,200,336 to Pavcnik et al. for a MULTIPLE-SIDED INTRALUMINAL MEDICAL DEVICE; U.S. application patent Ser. No. 10/642,372 of Pavcnik et al. for an IMPLANTABLE VASCULAR DEVICE, filed on Aug. 15, 2003; and U.S. application patent Ser. No. 10/828,716 of Case. et al. for an ARTIFICIAL VALVE PROSTHESIS WITH IMPROVED FLOW DYNAMICS, filed on Apr. 21, 2004; the entire disclosures of which are hereby incorporated into this disclosure for the purpose of describing suitable self-expandable medical devices for use with delivery systems according to the invention. FIG. 1 illustrates the delivery system 10 according to a first exemplary embodiment with two prosthetic valves 14, 16 disposed on the mounting regions 28, 30 of the elongate member 12. Each of the prosthetic valves 14, 16 include a graft member 40 and a self-expandable support frame 42.

In the illustrated embodiment, the sheath 18 is an elongate tubular member that is disposed over the elongate member 12 and the expandable medical devices 14, 16. In this first exemplary embodiment, the sheath 18 is circumferentially disposed about the elongate member 12 and the medical devices 14, 16 and has a length that is greater than a distance between a distal end of the distal mounting region 28 and a proximal end of the proximal mounting region 30. In this embodiment, the sheath 18 has a length that is substantially similar to the length of the elongate member without the distal end 22.

During deployment of the expandable medical devices 14, 16, the sheath 18 is retracted to remove a defining wall of the chambers 36, 38, thereby allowing the devices 14, 16 to expand. Following expansion of the devices 14, 16, the entire delivery system 10 can be withdrawn, and deployment of the devices 14, 16 is complete.

The sheath 18 can be formed of any suitable material or materials, including biocompatible plastics.

The chambers 36, 38 into which the expandable medical devices 14, 16 are disposed are separated by the length 44 of the intermediate portion 32. The length 44 can be any suitable length, and can be predetermined based upon a desired distance between the expandable medical devices 14, 16 following deployment. A predetermined length 44 can be based upon several considerations, including a known or expected distance between points of treatment within a body vessel. In one exemplary embodiment, a delivery system according to the invention includes two prosthetic valves disposed in chambers that are separated by a predetermined distance that is based on an expected distance between natural valves in a body vessel. In this configuration, a delivery system according to the invention can be used to deploy two prosthetic valves in positions that are separated by a distance that is substantially similar to a distance between natural valves in the vessel.

The delivery system 10 can be used as follows. First, a wireguide is navigated through a body vessel so that a portion of the wireguide is at or near a desired point of treatment within the vessel. Next, the delivery system 10 is advanced over the previously placed wireguide by passing the wireguide through the passageway 24. The delivery system 10 is advanced along the wireguide until at least one of the expandable medical devices is disposed adjacent a desired point of treatment. If the elongate member 12 includes an appropriate predetermined length 44 between chambers 36, 38, the medical devices 14, 16 can be disposed simultaneously at two different points of treatment within the body vessel. Once the delivery system is in a desired position, the sheath 18 is retracted to deploy the first expandable medical device 14. The sheath 18 is then further retracted to deploy the second expandable medical device 16. A repositioning of the delivery system within the body vessel can be conducted between deployment steps, if desired. Following deployment, the entire delivery system 10 is withdrawn from the vessel. A portion of the elongate member 12 is drawn through the deployed medical devices 14, 16, and the sheath 18 can be advanced back over the chambers 36, 38, if desired.

Figure 2:
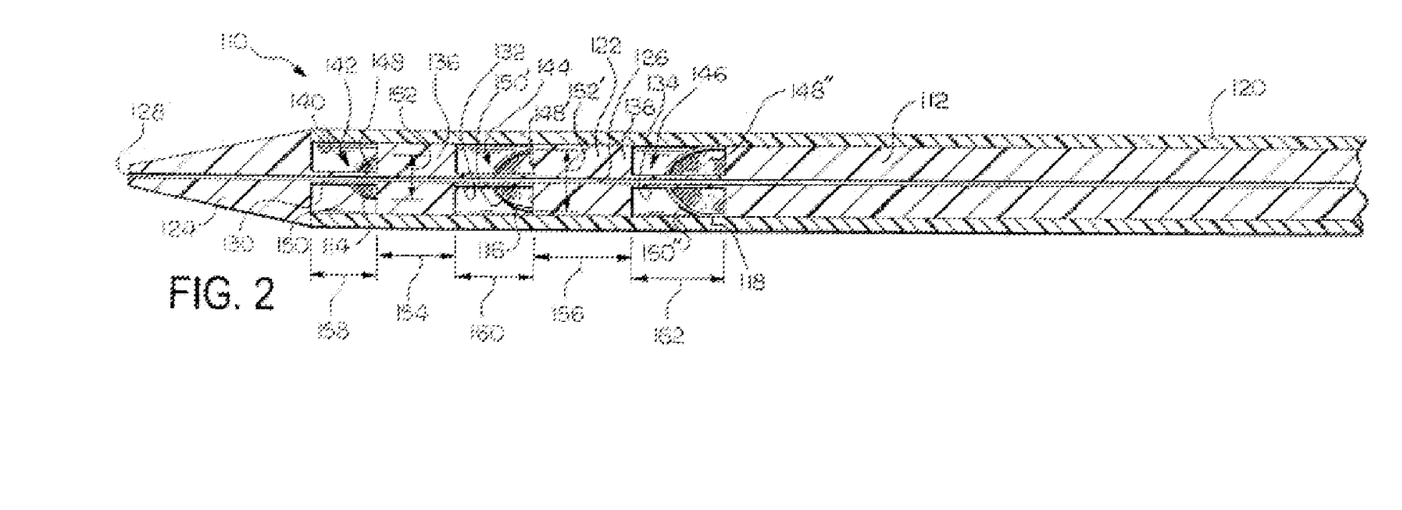
FIG. 2 is a sectional view of a delivery system according to a second exemplary embodiment of the invention.

FIG. 2 illustrates a delivery system 110 according to a second exemplary embodiment of the invention. The delivery system 110 of this embodiment is similar to the embodiment described above, except as indicated below. Accordingly, the delivery system 110 includes an elongate member 112, and first 114 and second 116 expandable medical devices. In this embodiment, the delivery system 110 includes a third expandable medical device 118. Similar to the first exemplary embodiment, a sheath 120 is disposed over the elongate member 112 and the medical devices 114, 116, 118. The elongate member 112 has a main body 122 and a tapered distal end 124, defines a passageway 126, and includes an opening 128 that provides access to the passageway 126.

The elongate member 112 defines mounting regions 130, 132, 134 that can receive the expandable medical devices 114, 116, 118. First 130 and second 132 mounting regions are separated by a first intermediate portion 136, and the second 132 and third 134 mounting regions are separated by a second intermediate portion 138. Each of the mounting regions 130, 132, 134 individually cooperate with an inner surface 140 of the sheath 120 to define a chamber 142, 144, 146 in which an expandable medical device 114, 116, 118 can be disposed.

In this embodiment, the expandable medical devices 114, 116, 118 differ from each other for at least one dimension. For example, each of the expandable medical devices 114, 116, 118 in this embodiment comprise an expandable prosthetic valve. The first prosthetic valve 114 includes a graft member 148 and an expandable support frame 150. The second prosthetic valve 116 includes a graft member 148' and an expandable support frame 150'. The third prosthetic valve 118 includes a graft member 148" and an expandable support frame 150". The valves 114, 116, 118 each have a resting diameter that differs from the resting diameter of the other valves. The first 114 and second 116 valves have first 152 and second 152' resting diameters. The third prosthetic valve 118 has a third resting diameter. It is understood that the first and second valves 114, 116 are illustrated as achieving their resting diameters 152, 152' while loaded in the delivery system 110 for illustration purposes only, and that this is not necessarily required or even desired. It is also understood that the medical devices 114, 116, 118 can differ for at least one dimension, and that such a difference in dimension is not required. Furthermore, for any set of devices, two or more can have the same or similar dimensions. Indeed, any suitable combination of devices, regardless of dimension, can be used.

The differing dimension of the expandable medical devices 114, 116, 118 can be selected based on features of the body vessel in which the medical devices 114, 116, 118 will be deployed. For example, the first medical device 114 can have a relatively small resting diameter 152 that makes it suitable for placement in a location of a body vessel having a relatively small inner diameter. Also, the third medical device 118 can have a relatively large resting diameter that makes it suitable for placement in a location of a body vessel having a relatively large inner diameter. The second medical device 116 can have an intermediate resting diameter that makes it suitable for placement in a location of a body vessel having an intermediate inner diameter. This configuration of the medical devices 114, 116, 118 is particularly desirable in applications in which multiple devices will be deployed along a length of a body vessel that has an inner diameter that increases along the length of the vessel. For example, prosthetic valves 114, 116, 118 can be deployed in a length of a vein that has a relatively small inner diameter at a distal portion and a relatively large inner diameter at a proximal portion, such as a saphenous vein in a human leg.

In this embodiment, the first intermediate portion 136 has a first predetermined length 154 and the second intermediate portion 138 has a second, different predetermined length 156. The lengths 154, 156 of the intermediate portions can be based upon known or expected distances between points of treatment within a body vessel, as described above. Also, the first chamber 142 has a first length 158. The second chamber 144 has a second length 160, and the third chamber 146 has a third length 162. Each of the lengths 158, 160, 162 is different than the other lengths 158, 160, 162. The length chosen for each chamber 142, 144, 146 can be based on a dimension of a medical device 114, 116, 118 that will be disposed in the chamber 142, 144, 146.

The delivery system 110 of this embodiment is used in the same manner as the first exemplary embodiment, described above. The sheath 120 is retracted to deploy each of the medical devices 114, 116, 118.

Delivery systems according to the invention can include any desired number of expandable medical devices. Also, the expandable medical devices in any particular delivery system can differ from all other expandable medical devices in the delivery system or from only one or some of the other expandable medical devices for a particular dimension, such as resting diameter.

Figure 3:
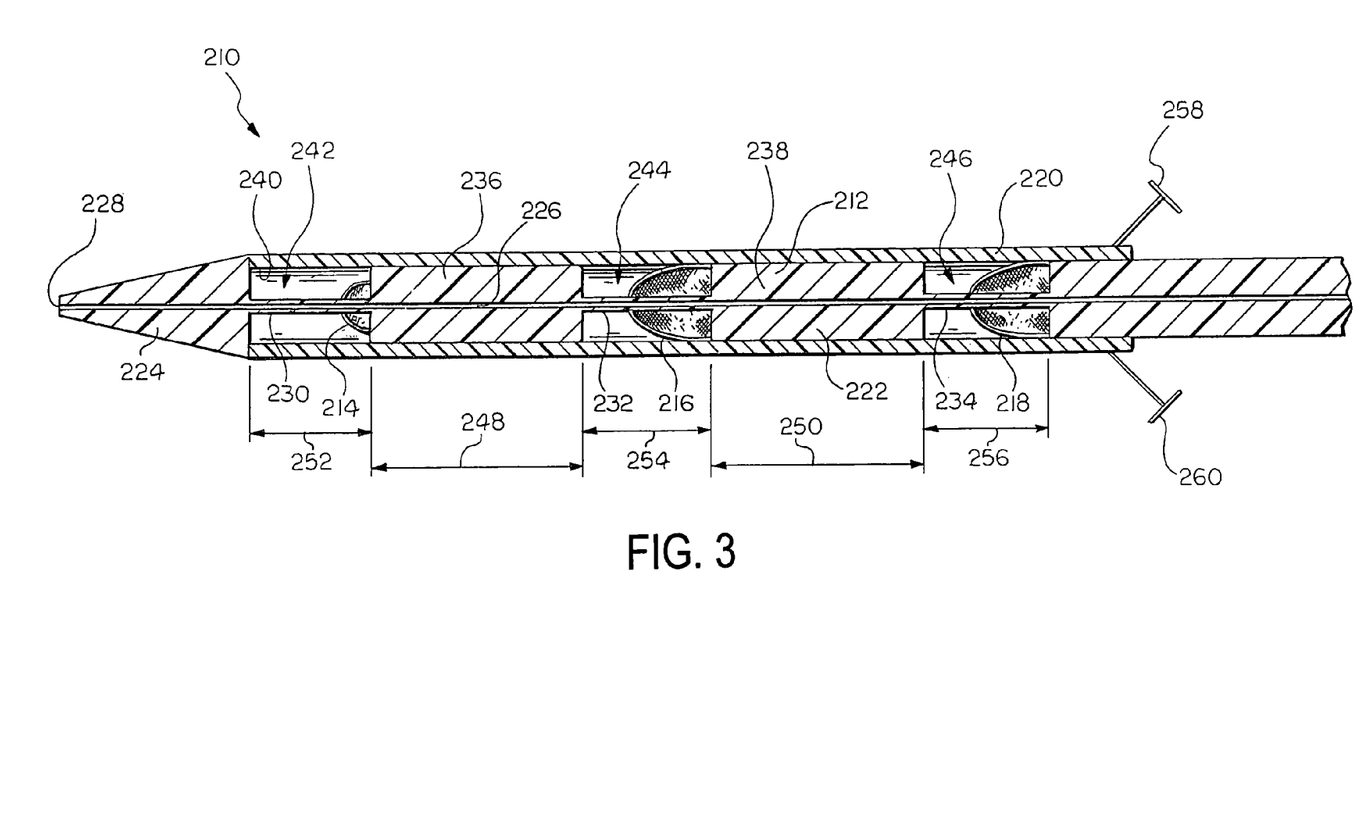
FIG. 3 is a sectional view of a delivery system according to a third exemplary embodiment of the invention.

FIG. 3 illustrates a delivery system 210 according to a third exemplary embodiment of the invention. The delivery system 210 of this embodiment is similar to the delivery system 110 of the second exemplary embodiment, illustrated in FIG. 2, except as described below. Accordingly, the delivery system 210 includes an elongate member 212 and first 214, second 216, and third 218 expandable medical devices. A sheath 220 is disposed over the elongate member 212 and the expandable medical devices 214, 216, 218. The elongate member 212 includes a main body 222, and a tapered distal end 224. The elongate member 212 defines a passageway 226, an opening 228, and mounting regions 230, 232, 234. Intermediate regions 236, 238 separate pairs of the mounting regions 230, 232, 234. The mounting regions 230, 232, 234 individually cooperate with an inner surface 240 of the sheath 220 to define chambers 242, 244, 246 in which the expandable medical devices 214, 216, 218 are disposed. In this embodiment, the length 248 of the first intermediate portion 236 is the same as the length 250 of the second intermediate portion 238. Also, the lengths 252, 254, 256 of the chambers 242, 244, 246 are substantially the same.

The sheath 220 in this embodiment has a length that is less than a distance between the proximal and distal ends of the elongate member 212. The sheath 220 has a length that allows it to extend over all of the chambers 242, 244, 246. Also, the sheath 220 includes pull tabs 258, 260. As such, the sheath 220 comprises a "peel-away" sheath, which allows for removal of the sheath 220 by pulling on the tabs 258, 260. A tearing of the sheath 220 results, which allows for removal of the sheath 220 without passing it over an end of the elongate member 212. This configuration can be desirable if the elongate member 212 will be used or might be used with another sheath, such as a full-length sheath.

Figure 4:
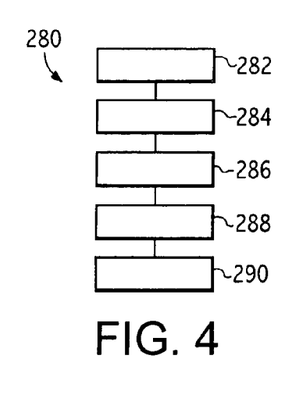
FIG. 4 is a block diagram of a method of assembling delivery systems according to the invention.

FIG. 4 illustrates a method 280 of assembling delivery systems according to the invention. In a step 282, an elongate member having first and second mounting regions is provided. In another step 284, first and second expandable medical devices are provided. In another step 286, a sheath is provided. In another step 288, the first and second expandable medical devices are disposed on the first and second mounting regions of the elongate member. The disposing can comprise two distinct disposing steps. In another step 290, the elongate member, with the first and second expandable medical devices disposed on the first and second mounting regions, respectively, is passed into the sheath at least until the sheath is disposed adjacent the first and second expandable medical devices.

The expandable medical devices of the delivery systems of the invention can be loaded in any suitable manner. Typically, the expandable medical devices will need to be compressed for placement within a delivery system. Accordingly, any suitable means for compressing the expandable medical devices can be used for loading purposes.

Figure 5:
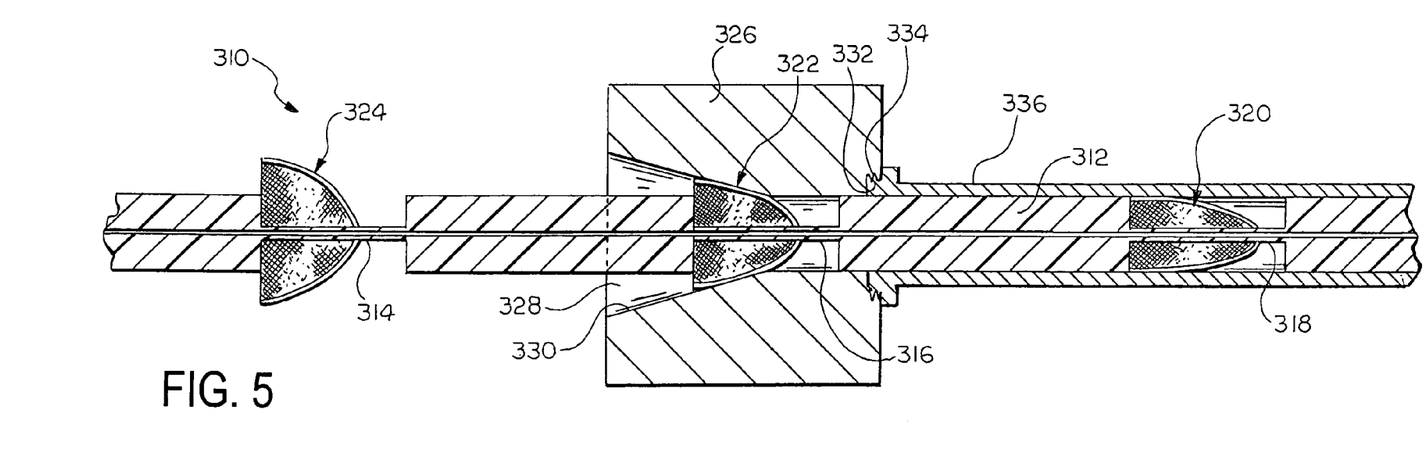
FIG. 5 is a sectional view of a delivery system during assembly in accordance with the invention.

FIG. 5 illustrates a delivery system 310 according to the invention during assembly. The delivery system 310 includes an elongate member 312 that defines mounting regions 314, 316, 318. Expandable medical devices 320, 322, 324 are disposed on the mounting regions 314, 316, 318.

A loading tool 326 that defines a chamber 328 with a tapered surface 330 comprises the means for compressing the expandable medical devices 320, 322, 324. Also, the loading tool 326 defines a connector, such as thread 332, that mates with a connector 334 on the sheath 336 to stabilize the apparatus during assembly of the delivery system 310. Any suitable connecting interface can be used between the loading tool 326 and the sheath 336, including interlocking threads, counterbores, clamps, mating tapers, and the like. A locking interface is considered beneficial, but is not necessary.

The delivery system 310 illustrated in FIG. 5 can be assembled as follows. Following provision of the elongate member 312, sheath 336, and expandable medical devices 320, 322, 324, the first expandable medical device 320 is placed on the first mounting region 318 of the elongate member 312. The portion of the elongate member 312 that includes the mounting region is then passed into the chamber 328 of the loading tool 326, and eventually into the connected sheath 336. This process is repeated for the second 322 and third 324 expandable medical devices until all medical devices are disposed in the chambers as described above, and are adjacent the sheath 336. Once all expandable medical devices 320, 322, 324 are loaded, the loading tool 326 can be disconnected from the sheath 336.

Any suitable structure can be used as the means for compressing the expandable medical devices. The structure chosen need only be able to compress the expandable medical devices to a sufficient degree to allow loading into the chamber and covering by the sheath. Connection to the sheath or any other component is considered optional.

Figure 6:
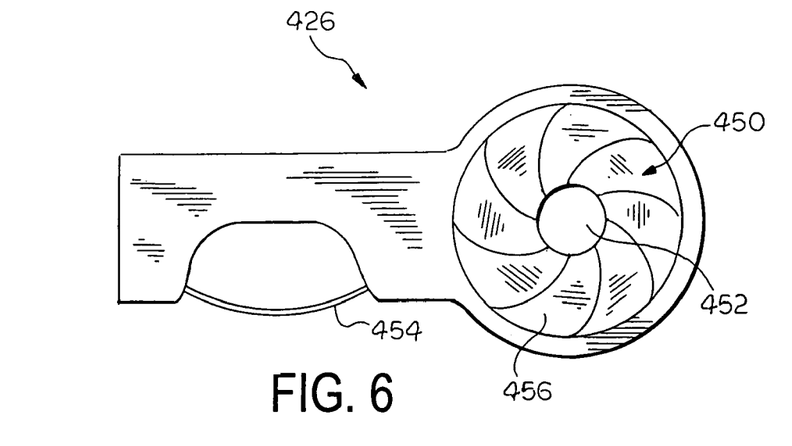
FIG. 6 is an elevational view of a compression device for use in assembly of delivery systems according to the invention.

FIG. 6 illustrates an alternate loading tool 426 that includes an iris valve 450 that forms an opening 452. To compress an expandable medical device, the handle 454 is activated, causing wall portions 456 to move and reduce the size of the opening 452. An expandable medical device disposed in the opening 452 is compressed as a result of the activation of the handle 454. The compressed expandable medical device can then be loaded into a delivery system according to the invention. The loading tool 426 is a suitable means for compressing expandable medical devices.

Figure 7:
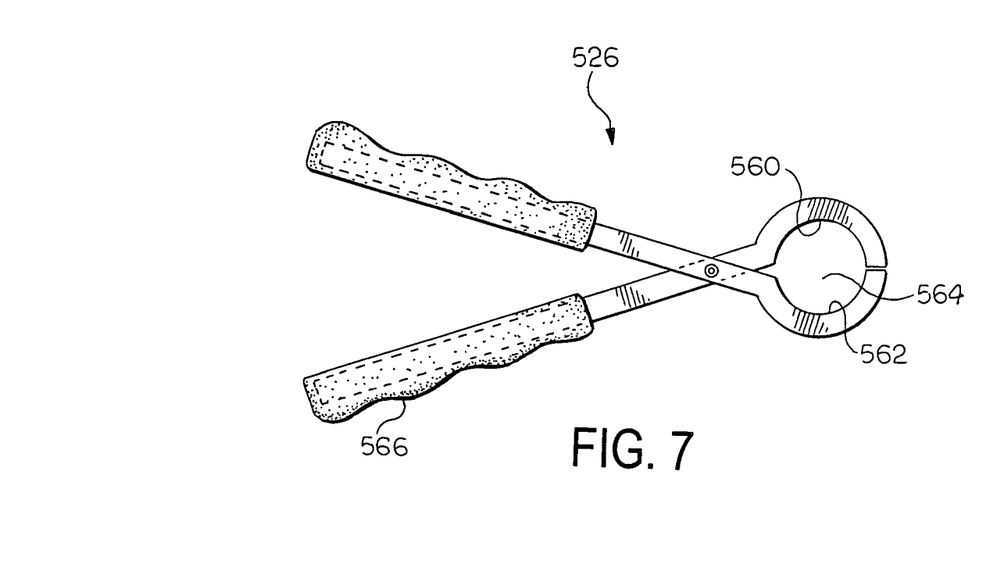
FIG. 7 is an elevational view of a compression device for use in assembly of delivery systems according to the invention.

FIG. 7 illustrates an alternative loading tool 526 that includes opposing surfaces 560, 562 that form an opening 564. In use, the handle 566 is activated, causing the opposing surfaces, 560, 562 to move toward each other and reduce the size of the opening 564. An expandable medical device disposed in the opening 564 is compressed as a result of the activation of the handle 566. The compressed expandable medical device can then be loaded into a delivery system according to the invention. The loading tool 526 is a suitable means for compressing expandable medical devices.

The invention also provides kits useful in techniques for implanting expandable medical devices within a body vessel. Kits according to the invention can be used for implantation of multiple expandable medical devices within one or more body vessels.

Figure 8:
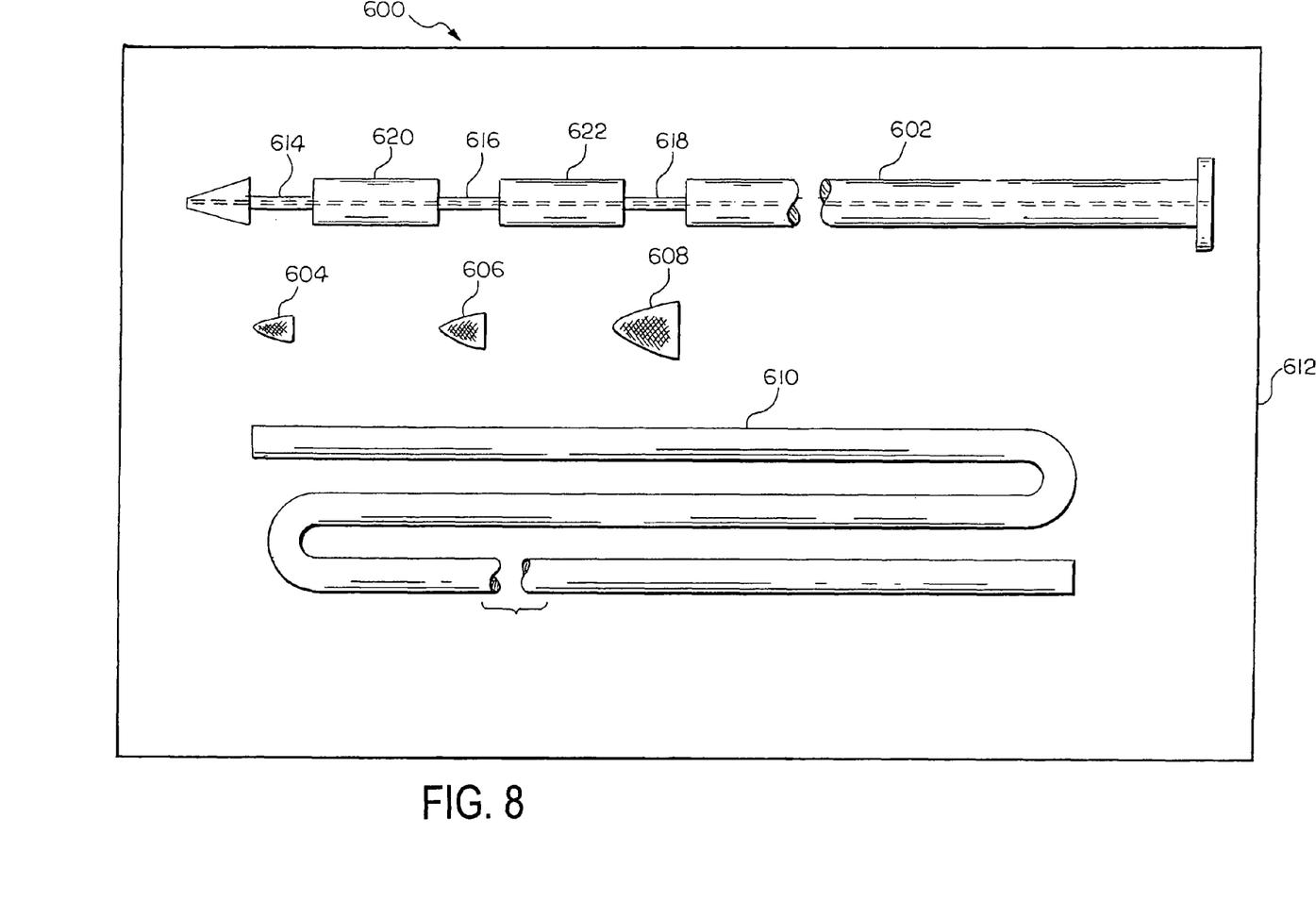
FIG. 8 is a schematic view of a kit according to an exemplary embodiment of the invention.

FIG. 8 is a schematic illustration of a kit 600 according to one exemplary embodiment of the invention. The kit 600 according to this embodiment includes an elongate member 602, first 604, second 606, and third 608 expandable medical devices, and a sheath 610. The components of the kit 600 are contained within a container 612.

The elongate member 602 can be any elongate member suitable for use in a delivery system according to the invention. The elongate member 602 advantageously defines first 614, second 616, and third 618 mounting regions. Also, first 620 and second 622 intermediate portions can each have a length based upon a known or expected distance between points of treatment for the first 604 and second 606 expandable medical devices, and between the second 606 and third 608 expandable medical devices, respectively.

The expandable medical devices 604, 606, 608 can comprise any suitable expandable medical devices, as described above. In kits according to exemplary embodiments of the invention, one or more of the expandable medical devices 604, 606, 608 comprise a prosthetic valve. Also, as illustrated in FIG. 8, the expandable medical devices 604, 606, 608 each include a dimension, such as a resting diameter, that is suitable for a particular point of treatment within a body vessel. In the illustrated embodiment, each of the three expandable medical devices 604, 606, 608 has a resting diameter that is different than the resting diameter for the other expandable medical devices 604, 606, 608. It is understood that expandable medical devices having the same dimensions can alternatively be included.

Kits according to the invention can include any suitable number of expandable medical devices, and any suitable combination of types, sizes, and configurations of expandable medical devices.

Figure 9:
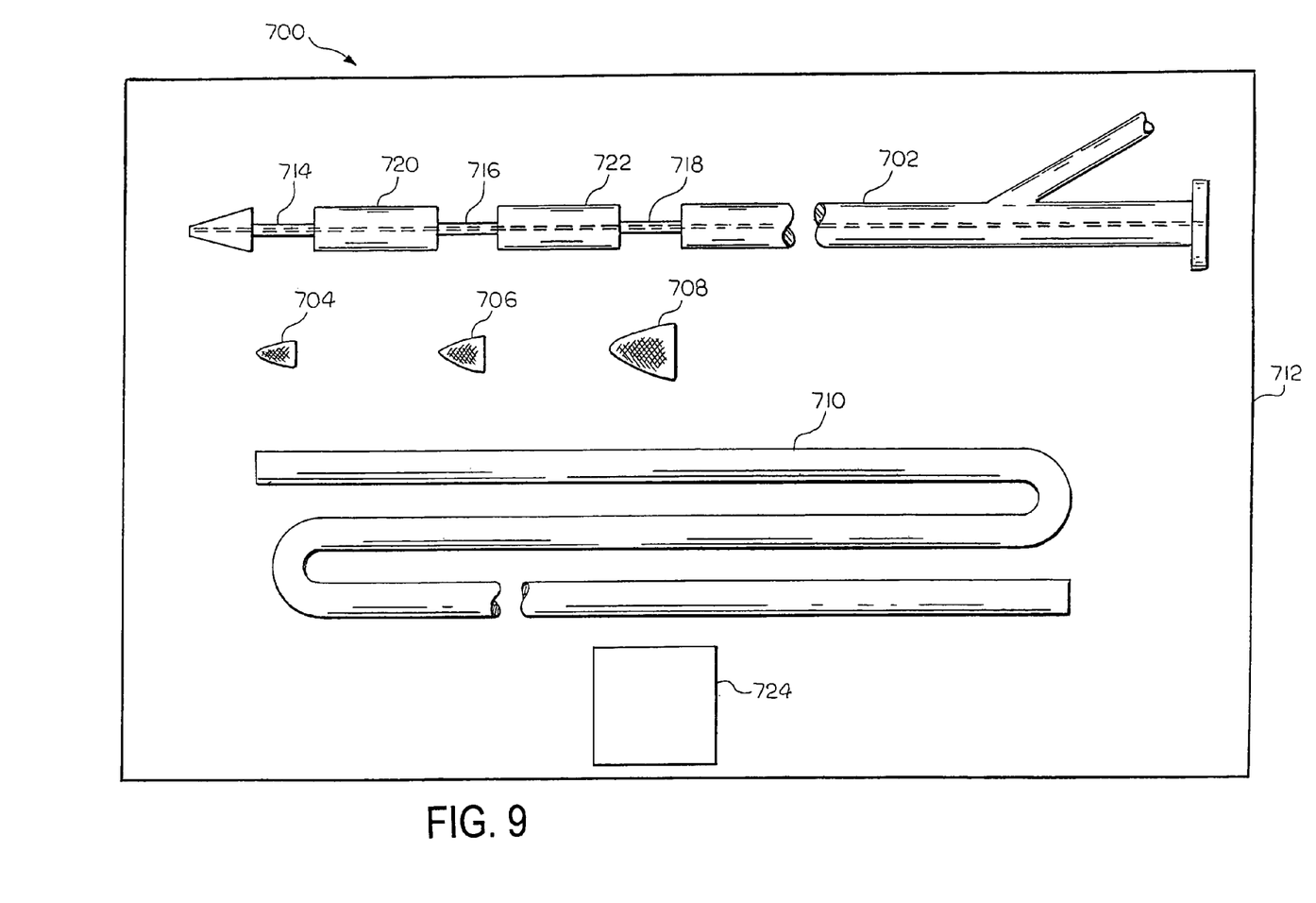
FIG. 9 is a schematic view of a kit according to an exemplary embodiment of the invention.

FIG. 9 illustrates a kit 700 according to another exemplary embodiment of the invention. The kit 700 of this embodiment is the same as the kit of the previous embodiment, except as described below. Thus, the kit 700 includes an elongate member 702, first 704, second 706, and third 708 expandable medical devices, and a sheath 710. The components of the kit 700 are contained within a container 712. The elongate member defines first 714, second 716, and third 718 mounting regions, and first 720 and second 722 intermediate portions.

In this embodiment, the kit 700 includes a means for compressing 724 the expandable medical devices 704, 706, 708 during loading and assembly of a delivery system with the components of the kit 700. The means for compressing 724 the expandable medical devices 704, 706, 708 can be any suitable means for compressing, including the loading tools described above and illustrated in FIGS. 5, 6, and 7.

Kits according to the invention can include any suitable number and type or types of expandable medical devices. The specific number and type(s) chosen for any particular kit will depend on several factors, including the type of treatment in which the kit will be used.

A kit according to one exemplary embodiment of the invention includes two expandable prosthetic valves. The valves have different resting diameters. An elongate member in the kit defines two mounting regions onto which the prosthetic valves can be disposed. The kit also includes a sheath that can be disposed adjacent the mounting regions and the prosthetic valves once disposed on the mounting regions. The kit can optionally include a means for compressing the prosthetic valves during loading and assembly of a delivery system with the components of the kit. A kit according to another exemplary embodiment is identical, except that it includes two expandable prosthetic valves with the same dimensions.

Figure 10:
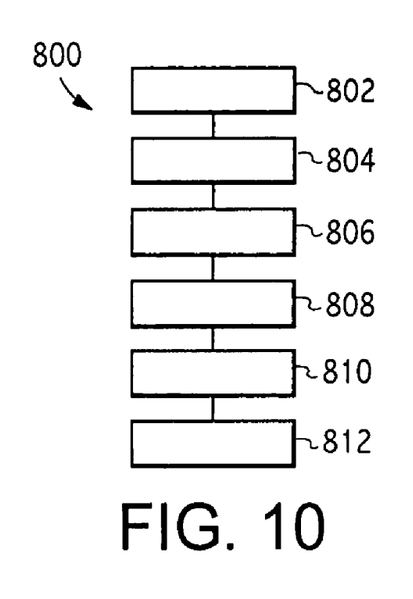
FIG. 10 is a block diagram illustrating a method of supplying medical devices in accordance with the invention.

The invention also provides methods of supplying medical devices for implantation within a body vessel. FIG. 10 illustrates an exemplary method 800 according to the invention.

In a first step 802 of this exemplary method 800, a supplier accepts a request for medical devices from a user. The user can be a physician, a hospital, a purchasing group or any other person or entity that may request medical devices.

In another step 804, the supplier collects data relating to first and second points of treatment within a body vessel. The data can relate to sizing of the vessel at the points of treatment, and can include measurement data such as inner diameters at the points of treatment. The data can be actual, predicted, or expected sizing data. Alternatively, the data can relate to positions of the points of treatment relative to the body vessel or other anatomical feature or features. The supplier can collect the data from any suitable source, including the requester and suitable reference sources.

In another step 806, the supplier selects a first medical device based on the data relating to the first point of treatment. For example, if the supplier is supplying prosthetic valves, the supplier can select a first prosthetic valve suitable for a known or expected inner diameter at the first point of treatment. In another step 808, the supplier selects a second medical device based on the data relating to the second point of treatment. Continuing with the prosthetic valve example, the supplier can select a second prosthetic valve suitable for a known or expected inner diameter at the second point of treatment.

In another step 810, the supplier assembles a delivery system comprising the first and second expandable medical devices. The assembly step 810 can include placing the first and second expandable medical devices on a suitable elongate member, such as a dilator or catheter, and can also include disposing a sheath over at least a portion of the elongate member and the expandable medical devices. The assembly step 810 can also include compressing the first and second expandable medical devices. The assembly step can also include placing the first and second expandable medical devices on the elongate member in a predetermined order. Continuing with the prosthetic valve example, it may be desirable to have the valves arranged with the first prosthetic valve, which may have a smaller resting diameter than the second prosthetic valve, at the distal mounting region on the elongate member. The order can be based on the data relating to the first and second points of treatment.

In another step 812, the supplier provides the delivery system to the user. The user in this step can be the same user who provided the initial request, an associate of the user who provided the initial request, or independent of the user who provided the initial request.

Figure 11:
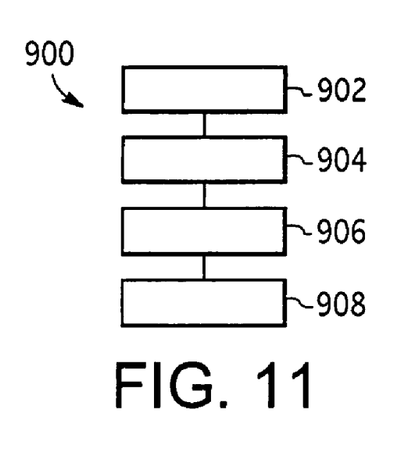
FIG. 11 is a block diagram illustrating a method of supplying medical devices in accordance with the invention.

FIG. 11 illustrates another exemplary method 900 according to the invention. In a step 902 of this method 900, a supplier accepts a request for expandable medical devices from a user. In another step 904, the supplier collects data relating to first and second points of treatment within a body vessel. In another step 906, the supplier selects first and second expandable medical devices based on the data relating to the first and second points of treatment, respectively. In another step 908, the supplier provides the first and second expandable medical devices to the user for assembly of a delivery system including the expandable medical devices by the user. The user can assemble the delivery system using an elongate member and sheath provided with the expandable medical devices, such as in a kit, or can use another suitable elongate member and another suitable sheath. The user can compress the expandable medical devices during assembly of the delivery system using a means for compressing expandable medial devices provided with the expandable medical devices, such as in a kit, or can use another suitable means for compressing expandable medical devices to compress the devices during assembly of the delivery system.

Figure 12:
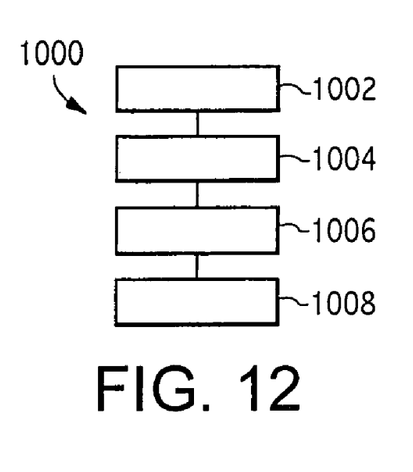
FIG. 12 is a block diagram illustrating a method of supplying medical devices in accordance with the invention.

FIG. 12 illustrates another exemplary method 1000 according to the invention. In a step 1002 of this method 1000, the supplier provides a plurality of expandable medical devices to a user. At least two of the plurality of expandable medical devices include a differing dimension. For example, a plurality of prosthetic valves can include at least two prosthetic valves with different resting diameters, or any other suitable dimension. In another step 1004, the supplier accepts a request for selection information from a user. In another step 1006, the supplier collects data relating to first and second points of treatment within a body vessel of interest to the user. The data can relate to sizing of the vessel at the points of treatment, and can include measurement data such as inner diameters of the vessel at the points of treatment. The data can be actual, predicted, or expected sizing data. Alternatively, the data can relate to positions of the points of treatment relative to the body vessel or other anatomical feature or features. The supplier can collect the data from any suitable source, including the user and suitable reference sources. In another step 1008, the supplier provides selection information to the user based on the data. The user can then select first and second expandable medical devices from the plurality of expandable medical devices based upon the selection information provided by the supplier. If desired, the user can then assemble a delivery system including the first and second expandable medical devices.

In one exemplary method according to the invention, the supplier provides a plurality of prosthetic valves to a user. At least two of the prosthetic valves have different resting diameters. In another step, the supplier accepts a request for selection information from the user. In another step, the supplier collects data relating to sizing of a body vessel at first and second points of treatment within the body vessel. The data advantageously are actual measurement data relating to the inner diameter of the body vessel at the points of treatment. In another step, the supplier provides selection information to the user based on the data. The selection information includes identifying information that allows the user to select suitable first and second prosthetic valves from the plurality of prosthetic valves. The identifying information can be, for example, a catalog number. The method can optionally include a step in which the supplier provides order information to the user. The order information relates to an order in which the first and second prosthetic valves should be placed within a delivery system. The user is able to use the selection information, and order information if included, to assemble a delivery system using suitable components.

The supplier can also supply the components for assembly of delivery systems, either with the plurality of prosthetic valves or separately. Also, the supplier can provide a means for compressing the prosthetic valves that the user can use during assembly of delivery devices. The supplier can provide the means for compressing either with the prosthetic valves or separately.

In all methods of supplying in which the supplier provides selection and/or order information, the subject information can be provided in any suitable manner, including, via oral or written communication, and via a computer interface, such as a database or other suitable interface. In one exemplary embodiment, the supplier provides a database with a world wide web interface. In this embodiment, the supplier provides the appropriate information when the database provides information in response to a query by the user. In all methods in which data are collected, the data can be collected in any suitable manner, including via oral and/or written communications. In one exemplary embodiment, the supplier collects data via a world wide web interface that allows a user to submit the data to the supplier, such as by completing an online form with appropriate fields.

The foregoing detailed description provides exemplary embodiments of the invention and includes the best mode for practicing the invention. These embodiments are intended only to serve as examples of the invention, and not to limit the scope of the invention, or its protection, in any manner.

I claim:

1. A delivery system for placing medical devices within a body vessel, said delivery system comprising:
   an elongate member comprising proximal and distal ends and having first and second mounting regions axially separated by a predetermined distance;
   a first expandable medical device disposed on the first mounting region;
   a second expandable medical device disposed on the second mounting region; and
   a sheath disposed over at least a portion of the elongate member and the first and second expandable medical devices;
   wherein the predetermined distance is based upon a desired distance between the first and second expandable medical devices following deployment from the mounting regions and upon one or more features of said body vessel.

2. A delivery system according to claim 1, wherein first expandable medical device has a first dimension suitable for a first point of treatment within said body vessel and the second expandable medical device has a second dimension suitable for a second point of treatment within said body vessel.

3. A delivery system according to claim 1, wherein at least one of the first and second expandable medical devices comprises a prosthetic valve.

4. A delivery system according to claim 1, wherein the first and second expandable medical devices comprise prosthetic valves.

5. A delivery system according to claim 4, wherein the predetermined distance is based upon an expected distance between first and second natural valves in said body vessel.

6. A delivery system according to claim 1, wherein the first and second expandable medical devices have different resting diameters.

7. A delivery system according to claim 1, wherein the sheath is slideably disposed over only a portion of the elongate member that includes the mounting regions.

8. A delivery system according to claim 7, wherein the sheath includes tabs that facilitate removal of the sheath from the elongate member.

9. A delivery system according to claim 1, wherein the first expandable medical device comprises a prosthetic valve having a first dimension suitable for a first point of treatment within said body vessel and the second expandable medical device comprises a prosthetic valve having a second dimension suitable for a second point of treatment within said body vessel.

10. A delivery system for placing multiple prosthetic valves within a body vessel, comprising:
   an elongate member comprising a proximal end, a distal end, a proximal mounting region, and a distal mounting region;
   a first prosthetic valve disposed on the proximal mounting region, the first prosthetic valve having a first dimension suitable for a first point of treatment within said body vessel;
   a second prosthetic valve disposed on the distal mounting region, the second prosthetic valve having a second dimension suitable for a second point of treatment within said body vessel and being different than the first dimension; and
   a sheath disposed over at least a portion of the elongate member and the first and second prosthetic valves;
   wherein the proximal and distal mounting regions are axially separated by a predetermined distance that is based upon one or more features of said body vessel.

11. A delivery system according to claim 10, wherein the sheath is circumferentially disposed about at least a portion of the elongate member and the first and second prosthetic valves.

12. A delivery system according to claim 10, wherein the elongate member defines a passageway that extends from the proximal end to the distal end.

13. A delivery system according to claim 10, wherein the elongate member defines a passageway that extends along only a portion of a length between the proximal and distal ends.

14. A delivery system according to claim 10, wherein the first and second prosthetic valves have different resting diameters.

15. A delivery system for placing medical devices within a body vessel, comprising an elongate member defining first and second mounting regions, a first prosthetic valve disposed on the first mounting region and having a first resting diameter, a second prosthetic valve disposed on the second mounting region and having a second, different resting diameter, and a sheath disposed over at least a portion of the elongate member and the first and second prosthetic valves; wherein the first and second mounting regions are axially separated by a predetermined distance that is based upon one or more features of said body vessel.

* * * * *

UNITED STATES PATENT AND TRADEMARK OFFICE
CERTIFICATE OF CORRECTION

| | | |
|---|---|---|
| PATENT NO. | : 8,292,938 B2 | Page 1 of 1 |
| APPLICATION NO. | : 11/210999 | |
| DATED | : October 23, 2012 | |
| INVENTOR(S) | : Brian C. Case | |

It is certified that error appears in the above-identified patent and that said Letters Patent is hereby corrected as shown below:

Title page, item [73] Assignee address reads --Bloomington, CO--. It should read --Bloomington, IN--.

Signed and Sealed this
Eighteenth Day of December, 2012

David J. Kappos
*Director of the United States Patent and Trademark Office*